(12) United States Patent
Ionkin

(10) Patent No.: US 8,115,378 B2
(45) Date of Patent: Feb. 14, 2012

(54) TETRA-SUBSTITUTED CHRYSENES FOR LUMINESCENT APPLICATIONS

(75) Inventor: Alex Sergey Ionkin, Kennett Square, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 802 days.

(21) Appl. No.: 11/960,807

(22) Filed: Dec. 20, 2007

(65) Prior Publication Data

US 2009/0162693 A1   Jun. 25, 2009

Related U.S. Application Data

(60) Provisional application No. 60/877,451, filed on Dec. 28, 2006.

(51) Int. Cl.
C09K 11/06 (2006.01)
H01L 51/54 (2006.01)
H05B 33/14 (2006.01)

(52) U.S. Cl. ........ 313/504; 313/506; 428/690; 428/917; 257/40; 257/E51.049

(58) Field of Classification Search .................. None
See application file for complete search history.

(56) References Cited

U.S. PATENT DOCUMENTS

| | | |
|---|---|---|
| 4,053,311 A | 10/1977 | Limburg et al. |
| 5,247,190 A | 9/1993 | Friend et al. |
| 5,408,109 A | 4/1995 | Heeger et al. |
| 6,670,645 B2 | 12/2003 | Grushin et al. |
| 6,852,429 B1 | 2/2005 | Li et al. |
| 6,875,524 B2 | 4/2005 | Hatwar et al. |
| 7,075,102 B2 | 7/2006 | Grushin et al. |
| 7,173,131 B2 | 2/2007 | Saitoh et al. |
| 7,358,409 B2 | 4/2008 | Saitoh et al. |
| 7,375,250 B2 | 5/2008 | Saitoh et al. |
| 7,491,450 B2 | 2/2009 | Okinaka et al. |
| 7,651,788 B2 | 1/2010 | Seo et al. |
| 7,709,104 B2 | 5/2010 | Saitoh et al. |
| 2002/0076576 A1 | 6/2002 | Li |
| 2003/0072966 A1 | 4/2003 | Hosokawa et al. |
| 2004/0102577 A1 | 5/2004 | Hsu et al. |
| 2004/0106003 A1 | 6/2004 | Chen et al. |
| 2004/0121184 A1 | 6/2004 | Thompson et al. |
| 2004/0127637 A1 | 7/2004 | Hsu et al. |
| 2005/0031898 A1 | 2/2005 | Li et al. |
| 2005/0064233 A1 | 3/2005 | Matsuura et al. |
| 2005/0158577 A1 | 7/2005 | Ishibashi et al. |
| 2005/0184287 A1 | 8/2005 | Herron et al. |
| 2005/0205860 A1 | 9/2005 | Hsu et al. |

(Continued)

FOREIGN PATENT DOCUMENTS

EP    443 861 B1    7/1995

(Continued)

OTHER PUBLICATIONS

Matsunami et al., JP(2006)-052323, machine assisted translation, publication date: Feb. 23, 2006.*

(Continued)

*Primary Examiner* — Jennifer Chriss
*Assistant Examiner* — Brett A Crouse

(57) ABSTRACT

This invention relates to electroluminescent 3,6,9,12-tetra-substituted chrysenes that are useful in electroluminescent applications. It also relates to electronic devices in which the active layer includes such a chrysene composition.

2 Claims, 1 Drawing Sheet

U.S. PATENT DOCUMENTS

| | | | |
|---|---|---|---|
| 2006/0033421 A1 | 2/2006 | Matsuura et al. | |
| 2006/0052641 A1* | 3/2006 | Funahashi | 564/426 |
| 2006/0113528 A1 | 6/2006 | Okinaka et al. | |
| 2006/0115678 A1 | 6/2006 | Saitoh et al. | |
| 2006/0121312 A1 | 6/2006 | Yamada et al. | |
| 2006/0152146 A1* | 7/2006 | Funahashi | 313/504 |
| 2006/0159838 A1 | 7/2006 | Kowalski et al. | |
| 2006/0194074 A1 | 8/2006 | Funahashi | |
| 2006/0210830 A1 | 9/2006 | Funahashi et al. | |
| 2006/0267488 A1 | 11/2006 | Saitoh et al. | |
| 2007/0063638 A1 | 3/2007 | Tokairin et al. | |
| 2007/0114917 A1 | 5/2007 | Funahashi | |
| 2007/0236137 A1 | 10/2007 | Funahashi | |
| 2007/0255076 A1 | 11/2007 | Ito et al. | |
| 2007/0292713 A9 | 12/2007 | Dobbs et al. | |
| 2007/0298530 A1 | 12/2007 | Feehery | |
| 2008/0049413 A1 | 2/2008 | Jinde et al. | |
| 2008/0071049 A1 | 3/2008 | Radu et al. | |
| 2008/0191614 A1 | 8/2008 | Kim et al. | |
| 2008/0233433 A1 | 9/2008 | Igarashi et al. | |
| 2008/0286605 A1 | 11/2008 | Takeda | |
| 2008/0303425 A1 | 12/2008 | Rostovtsev et al. | |
| 2009/0058279 A1 | 3/2009 | Takeda | |

FOREIGN PATENT DOCUMENTS

| | | | |
|---|---|---|---|
| EP | 1061112 A1 | 12/2000 | |
| EP | 1561794 A1 | 8/2005 | |
| EP | 2067766 A1 | 6/2009 | |
| EP | 2067767 A1 | 6/2009 | |
| JP | 07249490 A | 9/1995 | |
| JP | 200410550 A | 1/2004 | |
| JP | 2006151844 A | 6/2006 | |
| JP | 2006219392 A | 8/2006 | |
| JP | 2007186449 A | 7/2007 | |
| JP | 2009161470 A | 7/2009 | |
| KR | 20090046731 A | 5/2009 | |
| KR | 20090086015 A | 8/2009 | |
| KR | 20090086920 A | 8/2009 | |
| KR | 20090093897 A | 9/2009 | |
| WO | 03040257 A1 | 5/2003 | |
| WO | 03063555 A1 | 7/2003 | |
| WO | 2004016710 A1 | 2/2004 | |
| WO | 2005052027 A1 | 6/2005 | |
| WO | 2007021117 A1 | 2/2007 | |
| WO | 2007100096 A1 | 9/2007 | |
| WO | 2007105917 A1 | 9/2007 | |
| WO | 2007108666 A1 | 9/2007 | |
| WO | 2008149968 A1 | 12/2008 | |
| WO | 2009018009 A1 | 2/2009 | |
| WO | 2009028902 A2 | 3/2009 | |
| WO | 2009055628 A1 | 4/2009 | |
| WO | 2009028902 A3 | 6/2009 | |

OTHER PUBLICATIONS

Negishi et al., III.2.15 Palladium Catalyzed Conjugate Substitution, Handbook of Organopalladium Chemistry for Organic Synthesis, 2000, vol. 1:767-789.

John Markus, Photoconductive Cell, Electronics and Nucleonics Dictionary, 1966, pp. 470 & 476, McGraw-Hill.

Y. Wang, Photoconductive Polymers, Kirk-Othmer Encyclopedia of Chemical Technology, 4TH Edition, 1996, vol. 18:837-860.

Gustafsson et al., Flexible Light-Emitting Diodes Made From Suluble Conducting Polymers, Nature, 1992, vol. 357:477-479.

International Search Report, Korean Intellectual Property Office, Daejeon, Republic of Korea, Hyun Shik Oh, Authorized Officer, Dec. 24, 2010, in PCT/US2010/035364, PCT copending application.

Beckmann et al; Methyl reorientation in solid 3-ethylchrysene and 3-isopropylchrysene; 1998; vol. 12; pp. 251-256.

Kodomari et al; Selective Halogenation of Aromatic Hydrocarbons with Alumina-Supported Corrper (II) Halides, J. Org. Chem. 1988 vol. 53 pp. 2093-2094.

International Search Report, European Patent Office, Rijswijk NL, in PCT/2008/063811, PCT copending application 12/121,883, Csaba A. Nemes, Authorized Officer, Jul. 29, 2008.

International Search Report, European Patent Office, Rijswijk NL, in PCT/2008/065187, PCT copending application 12/129,753, Cecile Vanier, Authorized Officer, Feb. 10, 2008.

International Search Report, Korean Intellectual Property Office, Daejeon, Republic of Korea, in PCT/2009/065163, PCT copending application 13/120,001, Hyun Shik Oh, Authorized Officer, May 19, 2010.

International Search Report, Korean Intellectual Property Office, Daejeon, Republic of Korea, in PCT/2010/040578, PCT copending application, Hyun Shik Oh, Authorized Officer, Feb. 11, 2011.

International Search Report, Korean Intellectual Property Office, Daejeon, Republic of Korea, in PCT/2009/068956, PCT copending application 12/643,487, Hyun Shik Oh, Authorized Officer, Sep. 6, 2010.

International Search Report, Korean Intellectual Property Office, Daejeon, Republic of Korea, in PCT/2009/068928, PCT copending application 12/643,511, Hyun Shik Oh, Authorized Officer, Aug. 17, 2010.

International Search Report, European Patent Office, Rijswijk NL, in PCT/2008/065091, PCT corresponding application 12/129,760, Alina Sen, Authorized Officer, Oct. 23, 2008.

Mueller et al, Synthesis and Characterization of Soluble Oligo(9,10-anthrylene)s, Chem. Ber. 1994, 127, pp. 437-444.

* cited by examiner

TETRA-SUBSTITUTED CHRYSENES FOR LUMINESCENT APPLICATIONS

RELATED APPLICATION DATA

This application claims priority under 35 U.S.C. §119(e) from U.S. Provisional Application Ser. No. 60/877,451 filed on Dec. 28, 2006, which is incorporated by reference herein in its entirety.

BACKGROUND

1. Field of the Disclosure

This disclosure relates to electroluminescent 3,6,9,12-tetrasubstituted chrysenes. It also relates to electronic devices in which the active layer includes such a chrysene composition.

2. Description of the Related Art

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules such as anthracene, thiadiazole derivatives, and coumarin derivatives are known to show electroluminescence. Semiconductive conjugated polymers have also been used as electroluminescent components, as has been disclosed in, for example, U.S. Pat. Nos. 5,247,190, 5,408,109, and Published European Patent Application 443 861.

However, there is a continuing need for electroluminescent compounds, especially compounds that are soluble and are not limited to low intensity luminescence.

SUMMARY

Disclosed herein are electroluminescent 3,6,9,12-tetrasubstituted chrysenes that are useful in electroluminescent device applications. In some embodiments, the chrysenes are symmetrical, and in some the molecules are asymmetric. In one embodiment, the chrysene is tetrabromo substituted. Also disclosed electronic devices in which the active layer includes such a chrysene composition. A process for synthesizing a tetrabromo chrysene is also disclosed.

DETAILED DISCLOSURE

Definition of Terms

Figure 1:
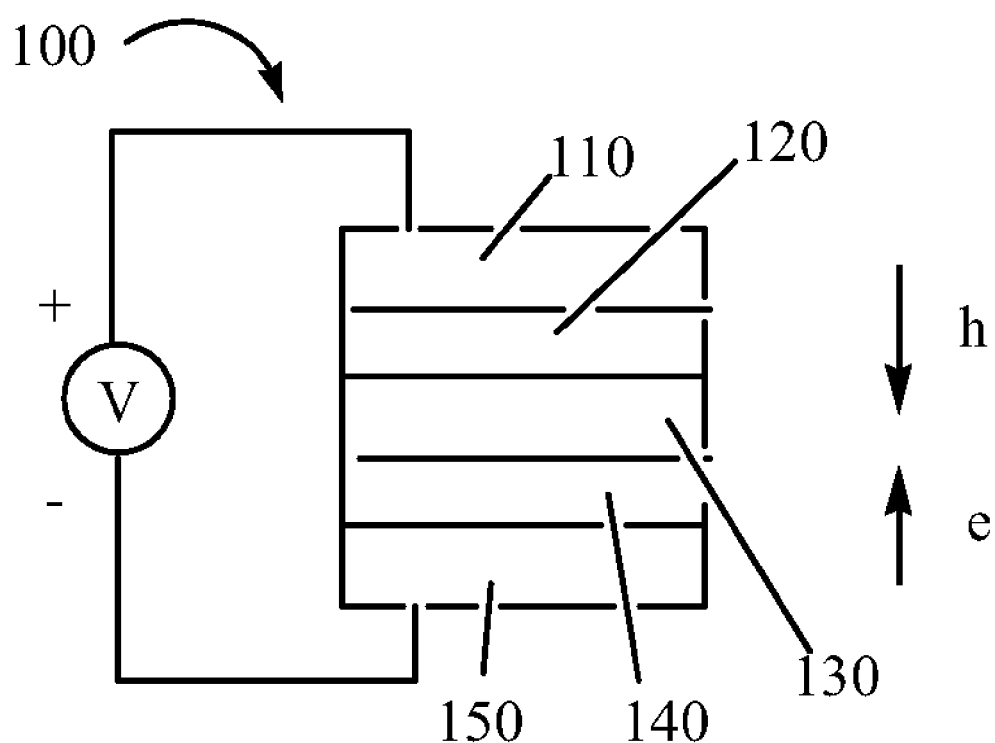
FIG. 1 is a schematic diagram of a light-emitting device (LED).

As used herein, the term "compound" is intended to mean an electrically uncharged substance made up of molecules that further consist of atoms, wherein the atoms cannot be separated by physical means. The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond). The term "photoactive" refers to any material that exhibits electroluminescence and/or photosensitivity.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The IUPAC numbering system is used throughout, where the groups from the Periodic Table are numbered from left to right as 1-18 (CRC Handbook of Chemistry and Physics, 81$^{st}$ Edition, 2000).

DESCRIPTION OF EMBODIMENTS

One aspect of the present disclosure is a composition of Formula I:

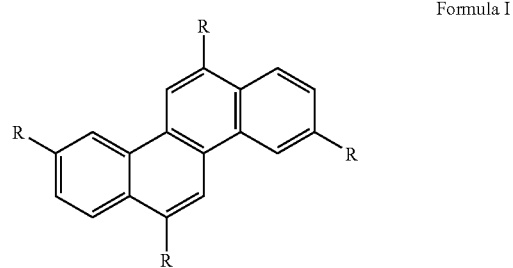

Formula I wherein each R is independently selected from the group consisting of alkyl, aryl, heteroaryl, diarylamino, dialkylamino, aryl(alkyl)amino, arylthio, alkylthio, aryleleno, alkylseleno, aryloxy, alkoxy, dialkylphosphino, diarylphosphino, dialkylphosphoryl, diarylphosphoryl, and thiophosphoryl.

Suitable alkyl groups include $C_1$-$C_{20}$ substituted and unsubstituted alkyls. Suitable aryls include substituted and unsubstituted phenyl and naphthyl groups. Suitable heteroaryls include substituted and unsubstituted pyridines, quinolines, isoquinolines, pyrimidines, pyrazines, pyridazines, purines, indoles, isoindoles, benzothiophenes, quinazolines, cinnolines, benzofurans, benzimidazoles, quinoxalines and inolines. Suitable diarylaminos, diarylphosphinos, and diarylphosphoryls include amino, phosphino, and phosphoryl groups, respectively, comprising two substituted or unsubstituted phenyl groups. Suitable dialkylaminos, dialkylphosphinos, and dialkylphosphoryls include amino, phosphino, and phosphoryl groups, respectively, comprising two substituted or unsubstituted $C_1$-$C_{10}$ alkyl groups. Suitable aryl(alkyl)amino groups include amino groups comprising one substituted or unsubstituted phenyl group and one substituted or unsubstituted $C_1$-$C_{10}$ alkyl group. Suitable arylthio (or arylseleno) groups include thio (or seleno) groups comprising one substituted or unsubstituted phenyl group. Suitable alkylthio (or alkylseleno) groups include thio (or seleno) groups comprising one $C_1$-$C_{10}$ substituted or unsubstituted alkyl group. Suitable aryloxy groups include oxy groups comprising one substituted or unsubstituted phenyl group. Suitable alkoxy groups include oxy groups comprising a substituted or unsubstituted $C_1$-$C_{10}$ alkyl group.

Suitable substituents for the aryl groups include halo, amino, silyl, and $C_1$-$C_{10}$ alkyl groups. Suitable substituents for the alkyl groups include amino, halo and silyl groups.

The chrysenes disclosed are readily prepared by the Suzuki coupling of the corresponding 3,6,9,12-tetra-bromochrysene using standard palladium catalysts. Typical Suzuki reactions are described by Negishi, et al., Palladium-catalyzed cross-coupling substitution. Handbook of Organopalladium Chemistry for Organic Synthesis (2002), 1 767-789. As illustrated in Examples 2 and 3, below, the tetra-aryl chrysenes are readily prepared by reacting 3,6,9,12-tetrabromochrysene with a slight excess of an arylboronic acid in the presence of a Pd(0) catalyst (e.g., tris(dibenzylideneacetone)dipalladium (0)), di-tert-butyl-trimethylsilylmethylphosphane, 1,4-dioxane and a base (e.g., cesium carbonate). Suitable reaction times are from about 5-100 hours. Suitable temperatures are from about 24-140° C. Suitable solvents include dioxanes, toluene, and tetrahydrofuran. Isolation and purification of the tetra-substituted chrysene product can be accomplished by techniques such as extraction, chromatography, crystallization, sublimation, used alone or in combination.

It has been found that 3,6,9,12-tetrabromochrysene, a useful starting material for the preparation of the compounds of Formula I, can be readily prepared by reacting chrysene with bromine in a polar, aprotic solvent at 60° C.-200° C. for 3 hr-7 days. The preferred solvent is trimethylphosphate.

The chrysene compounds disclosed herein are neutral and non-ionic, and can be sublimed intact. Thin films of these materials obtained via vacuum deposition exhibit good to excellent electroluminescent properties. Introduction of substitutents onto the chrysene ring can increase both the stability and volatility of the chrysene. As a result, vacuum deposition can be carried out at relatively low temperatures to avoid decomposition of the compound.

Electronic Device

A generic organic light emitting diode (OLED) consists of several thin-film layers: (1) a transparent anode, usually indium tin oxide (ITO) on glass, (2) a hole transport material, (3) a luminescent material, (4) an electron transport material, and (5) a metallic cathode (e.g. Al, Al/LiF, or a low work-function metal alloy). The electrons and holes are injected from the cathode and anode into the device, and are then induced to recombine within the luminescent layer by the use of hole-transport and electron-transport layers. Recombination of electrons and holes generates an excited state of the molecular species that emits light.

A typical OLED device structure is shown in FIG. 1. The device 100 has an anode layer 110 and a cathode layer 150. Adjacent to the anode is a layer 120 comprising hole transport material. Adjacent to the cathode is a layer 140 comprising an electron transport/anti-quenching material. Between the hole transport layer and the electron transport/anti-quenching layer is the photoactive layer 130. As an option, devices frequently use another electron transport layer 160 (not shown), next to the cathode. Layers 120, 130, 140, and 160 are individually and collectively referred to as the active layers.

Depending upon the application of the device 100, the photoactive layer 130 can be a light-emitting layer that is activated by an applied voltage (such as in a light-emitting diode or light-emitting electrochemical cell), or a layer of material that responds to radiant energy and generates a signal with or without an applied bias voltage (such as in a photo-detector). Examples of photodetectors include photoconductive cells, photoresistors, photoswitches, phototransistors, and phototubes, and photovoltaic cells, as these terms are described in Markus, John, *Electronics and Nucleonics Dictionary*, 470 and 476 (McGraw-Hill, Inc. 1966).

Triarylmethane derivatives are particularly useful as the hole transport layer 120, and as a charge conducting host in the photoactive layer, 130. Examples of hole transport materials for layer 120 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino) phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl] pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), N,N'-bis (naphthalen-1-yl)-N,N'-bis-(phenyl)benzidine (α-NPB), and porphyrinic compounds, such as copper phthalocyanine. Commonly used hole transporting polymers are polyvinylcarbazole, (phenylmethyl)-polysilane, and polyaniline. It is also possible to obtain hole transporting polymers by doping hole transporting molecules such as those mentioned above into polymers such as polystyrene and polycarbonate.

The other layers in the device can be made of any materials that are known to be useful in such layers.

The anode 110, is an electrode that is particularly efficient for injecting positive charge carriers. It can be made of, for example, materials containing a metal, mixed metal, alloy, metal oxide or mixed-metal oxide, or it can be a conducting polymer, or mixtures thereof. Suitable metals include the Group 11 metals, the metals in Groups 4-6, and the Group 8-10 transition metals. If the anode is to be light-transmitting, mixed-metal oxides of Groups 12, 13 and 14 metals, such as indium-tin-oxide, are generally used. The anode 110 can also comprise an organic material such as polyaniline as described in "Flexible light-emitting diodes made from soluble conducting polymer," *Nature* vol. 357, pp 477-479 (11 Jun. 1992). At least one of the anode and cathode is desirably at least partially transparent to allow the generated light to be observed.

Examples of the photoactive layer 130 include all known electroluminescent materials. These electroluminescent complexes can be used alone, or doped into charge-carrying hosts, as noted above. The tetra-substituted chrysenes of Formula I of the present invention, in addition to being useful as emissive dopants in the photoactive layer, can also act as charge carrying hosts for other emissive dopants in the photoactive layer 130.

Examples of additional electron transport materials which can be used in layer 140 include metal chelated oxinoid compounds, such as tris(8-hydroxyquinolato)aluminum ($Alq_3$); bis(2-methyl-8-quinolinolato)(para-phenyl-phenolato)aluminum(III) (BAlQ); and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ), and 1,3,5-tri(phenyl-2-benzimidazole) benzene (TPBI); quinoxaline derivatives such as 2,3-bis(4-fluorophenyl)quinoxaline; phenanthroline derivatives such as 9,10-diphenylphenanthroline (DPA) and 2,9-dimethyl-4,7- diphenyl-1,10-phenanthroline (DDPA); and mixtures thereof. Layer 140 can function both to facilitate electron transport, and also serve as a buffer layer or confinement layer to prevent quenching of the exciton at layer interfaces. Preferably, this layer promotes electron mobility and reduces exciton quenching.

The cathode 150, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds, LiF, and $Li_2O$ can also be deposited between the organic layer and the cathode layer to lower the operating voltage.

It is known to have other layers in organic electronic devices. For example, there can be a layer (not shown) between the anode 110 and hole transport layer 120 to control the amount of positive charge injected and/or to provide bandgap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, the hole transport layer 120, the electron transport layers 140 and 160, or cathode layer 150, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

The device can be prepared by a variety of techniques, including sequential vapor deposition of the individual layers on a suitable substrate. Substrates such as glass, plastics, and metals can be used. Conventional vapor deposition techniques can be used, such as thermal evaporation, chemical vapor deposition, and the like. Alternatively, the organic layers can be applied from solutions or dispersions in suitable solvents, using conventional coating or printing techniques, including but not limited to spin-coating, dip-coating, roll-to-roll techniques, ink-jet printing, screen-printing, gravure printing and the like. In general, the different layers will have the following range of thicknesses: anode 110, 500-5000 Å, preferably 1000-2000 Å; hole transport layer 120, 50-2000 Å, preferably 200-1000 Å; photoactive layer 130, 10-2000 Å, preferably 100-1000 Å; electron transport layers 140 and 160, 50-2000 Å, preferably 100-1000 Å; cathode 150, 200-10000 Å, preferably 300-5000 Å. The location of the electron-hole recombination zone in the device, and thus the emission spectrum of the device, can be affected by the relative thickness of each layer. Thus the thickness of the electron-transport layer is desirably chosen so that the electron-hole recombination zone is in the light-emitting layer. The desired ratio of layer thicknesses will depend on the exact nature of the materials used.

The present disclosure also relates to an electronic device comprising at least one photoactive layer positioned between two electrical contact layers, wherein the at least one layer of the device includes the tetra-substituted chrysene of Formula 1. Devices frequently have additional hole transport and electron transport layers.

The chrysene compounds of the disclosure are particularly useful as the photoactive material in layer 130, or as electron transport material in layer 140. Preferably the chrysene compounds of the invention are used as the light-emitting material in diodes. Additional materials can be present in the emitting layer with the tetra-substituted chrysene. For example, a fluorescent dye can be present to alter the color of emission. A diluent can also be added and such diluent can be a charge transport material or an inert matrix. A diluent can comprise polymeric materials, small molecule or mixtures thereof. A diluent can act as a processing aid, can improve the physical or electrical properties of films containing the tetra-substituted chrysene, can decrease self-quenching in the chrysenes described herein, and/or can decrease the aggregation of the chrysenes. Non-limiting examples of suitable polymeric materials include poly(N-vinyl carbazole), polyfluorene, and polysilane. Non-limiting examples of suitable small molecules include 4,4'-N,N'-dicarbazole biphenyl, bis(2-methyl-8-quinolinolato)(para-phenyl-phenolato)aluminum(III) (BAlQ); and tertiary aromatic amines. When a diluent is used, the chrysene is generally present in a small amount. In one embodiment, the chrysene of Formula I is less than 20% by weight, based on the total weight of the layer. In another embodiment, the tetra-substituted chrysene of Formula I is less than 10% by weight, based on the total weight of the layer.

To achieve a high efficiency LED, the HOMO (highest occupied molecular orbital) of the hole transport material desirably aligns with the work function of the anode, and the LUMO (lowest un-occupied molecular orbital) of the electron transport material desirably aligns with the work function of the cathode. Chemical compatibility and sublimation temperature of the materials are also important considerations in selecting the electron and hole transport materials.

It is understood that the efficiency of devices made with the tetra-substituted chrysenes of the invention, can be further improved by optimizing the other layers in the device. For example, more efficient cathodes such as Ca, Ba or LiF can be used. Shaped substrates and novel hole transport materials that result in a reduction in operating voltage or increase quantum efficiency are also applicable. Additional layers can also be added to tailor the energy levels of the various layers and facilitate electroluminescence.

The chrysenes of the disclosure often are phosphorescent and photoluminescent and can be useful in applications other than OLEDs, such as oxygen sensitive indicators and as phosphorescent indicators in bioassays.

EXAMPLES

The following examples illustrate certain features and advantages of the present invention. They are intended to be illustrative of the invention, but not limiting. All percentages are by weight, unless otherwise indicated.

Tris(dibenzylideneacetone) dipalladium was purchased from Alfa-Aesar (Ward Hill, Mass.).

MPMP was prepared in a manner similar to that for bis(4-diethylamino-2-methylphenyl)phenylmethane, as described in U.S. Pat. No. 4,053,311 (Example 1), except that p-tolualdehyde was substituted for benzaldehyde.

All other reagents were purchased and used as received from Sigma-Aldrich Co. (Milwaukee, Wis.), unless otherwise indicated.

Example 1

3,6,9,12-Tetrabromo-chrysene

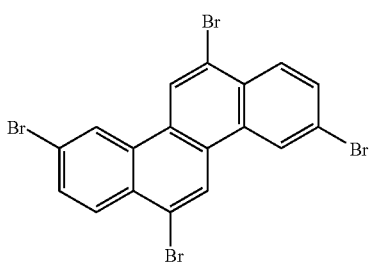

Bromine (85 g, 0.53 mol) in trimethylphosphate (100 ml) was added dropwise to a stirred solution of chrysene (20.0 g, 0.0876 mol) dissolved in trimethylphosphate (300 ml) at 60° C. The reaction temperature was slowly increased to 100° C. and kept for 3 days at that temperature. The resultant precipitate was filtered and washed with methanol (2×100 ml). Yield of 3,6,9,12-tetrabromo-chrysene was 39.14 g (82.14%). Direct probe GC/MS Exact mass found=539.74 g/mole.

Example 2

3,6,9,12-Tetrakis-(4-tert-butyl-phenyl)-chrysene

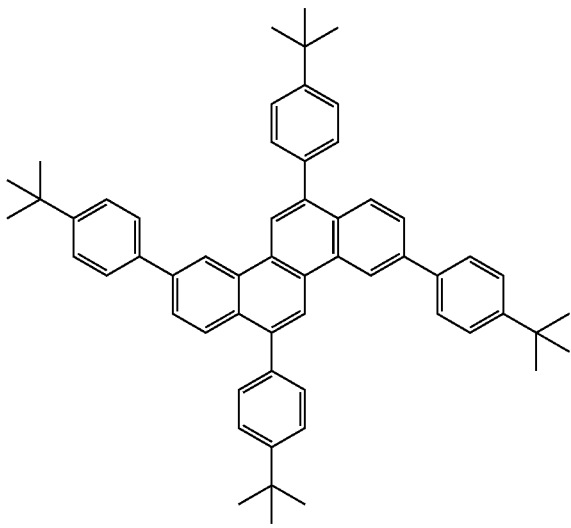

3,6,9,12-Tetrabromo-chrysene (5.0 g, 0.00919 mol), 4-tert-butylphenylboronic acid (9.82 g, 0.0552 mol), tris(dibenzylideneacetone) dipalladium(0) (1.26 g, 0.00138 mol), di-tert-butyl-trimethylsilylmethyl-phosphane (0.62 g, 0.02670 mol), cesium carbonate (17.97 g, 0.0552 mol) and 1,4-dioxane (100 ml) were refluxed for 48 h. The resultant mixture was poured into 200 ml of water and extracted twice by 200 ml of methylene chloride. The organic phase was dried over magnesium sulfate overnight and filtered. The solvent was removed on a rotary evaporator and the residue was purified by chromatography on silica gel with petroleum ether/ethyl ether (10/0.5) as eluant. Yield of 3,6,9,12-tetrakis-(4-tert-butyl-phenyl)-chrysene was 2.05 g (30%) as a white solid with m.p. 376.48° C. $^1$H NMR (CD$_2$Cl$_2$) 1.30 (s, 9H, t-Bu), 1.35 (s, 9H, t-Bu), 1.50 (s, 18H, t-Bu), 7.60-9.20 (m, 24H, arom.-H). GC/MS (direct probe): Exact mass found: 756.47. The pattern of the substitution of the chrysene ring was confirmed by X-ray analysis.

This compound shows blue photoluminescence in both solution and solid state. In toluene solution, the photoluminescence quantum yield is 0.49.

Example 3

3,6,9,12-Tetrakis-(2,4,6-trimethyl-phenyl)-chrysene

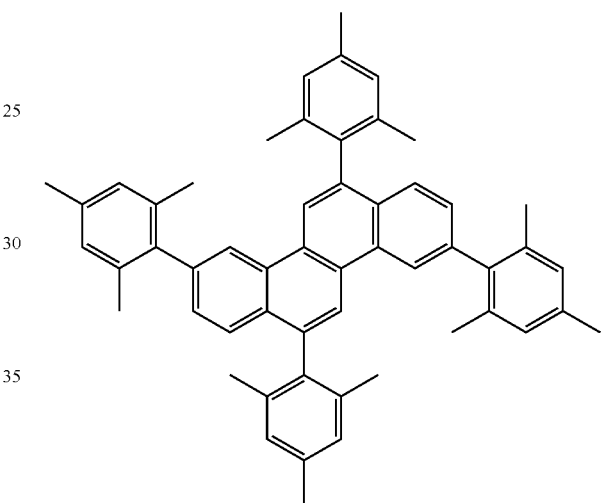

3,6,9,12-Tetrabromo-chrysene (5.0 g, 0.00919 mol), mesitylboronic acid (10.0 g, 0.0610 mol), tris(dibenzylideneacetone) dipalladium (0), (1.40 g, 0.00153 mol), di-tert-butyl-trimethylsilylmethyl-phosphane (0.68 g, 0.00293 mol), cesium carbonate (19.87 g, 0.0610 mol) and 1,4-dioxane (100 ml) were refluxed for 48 h. The resultant mixture was poured into 200 ml of water and extracted twice by 200 ml of methylene chloride. The organic phase was dried over magnesium sulfate overnight and filtered. The solvent was removed on a rotary evaporator. The residue was purified by chromatography on silica gel with petroleum ether/ethyl ether (10/0.5) as eluant. Yield of 3,6,9,12-tetrakis-(2,4,6-trimethyl-phenyl)-chrysene was 1.46 g (23%) as a white solid with no m.p. below 300° C. $^1$H NMR (C$_6$D$_6$) 2.10-2.55 (m, 36H, Me), 7.05-9.20 (m, 16H, arom.-H). GC/MS (direct probe): Exact mass Found: 700.41.

Example 4

OLED devices were fabricated by the thermal evaporation technique. The base vacuum for all of the thin film deposition was in the range of 10$^{-6}$ torr. The deposition chamber was capable of depositing eight different films without the need to break the vacuum.

Patterned indium tin oxide (ITO) coated glass substrates from Thin Film Devices, Inc were used. These ITO's are based on Corning 1737 glass coated with 1400 Å ITO coating, with sheet resistance of 30 ohms/square and 80% light transmission. The patterned ITO substrates were then cleaned ultrasonically in aqueous detergent solution. The substrates were then rinsed with distilled water, followed by isopropanol, and then degreased in toluene vapor.

The cleaned, patterned ITO substrate was then loaded into the vacuum chamber and the chamber was pumped down to $10^{-6}$ torr. The substrate was then further cleaned using an oxygen plasma for about 5 min. After cleaning, multiple layers of thin films were then deposited sequentially onto the substrate by thermal evaporation. Patterned metal electrodes (Al or LiF/Al) or bipolar electrode were deposited through a mask. The thickness of the film was measured during deposition using a quartz crystal monitor. All film thickness reported in the Examples are nominal, calculated assuming the density of the material deposited to be one. The completed OLED device was then taken out of the vacuum chamber and characterized immediately under flowing nitrogen without encapsulation.

The OLED samples were characterized by measuring their (1) current-voltage (I-V) curves, (2) electroluminescence radiance versus voltage, and (3) electroluminescence spectra versus voltage. The I-V curves were measured with a Keithley Source-Measurement Unit Model 237. The electroluminescence radiance (in the unit of $cd/m^2$) vs. voltage was measured with a Minolta LS-110 luminescence meter, while the voltage was scanned using the Keithley SMU. The electroluminescence spectrum was obtained by collecting light using an optical fiber, through an electronic shutter, dispersed through a spectrograph, and then measured with a diode array detector. All three measurements were performed at the same time and controlled by a computer. The efficiency of the device at certain voltage is determined by dividing the electroluminescence radiance of the LED by the current density needed to run the device. The unit is in cd/A.

Table I summarizes device configuration and efficiency of OLED devices fabricated using materials disclosed in the present invention. MPMP is the hole transport material, DPA is the electron transport material, and AlQ is the electron injection material. Their molecular structures are shown in the structures below.

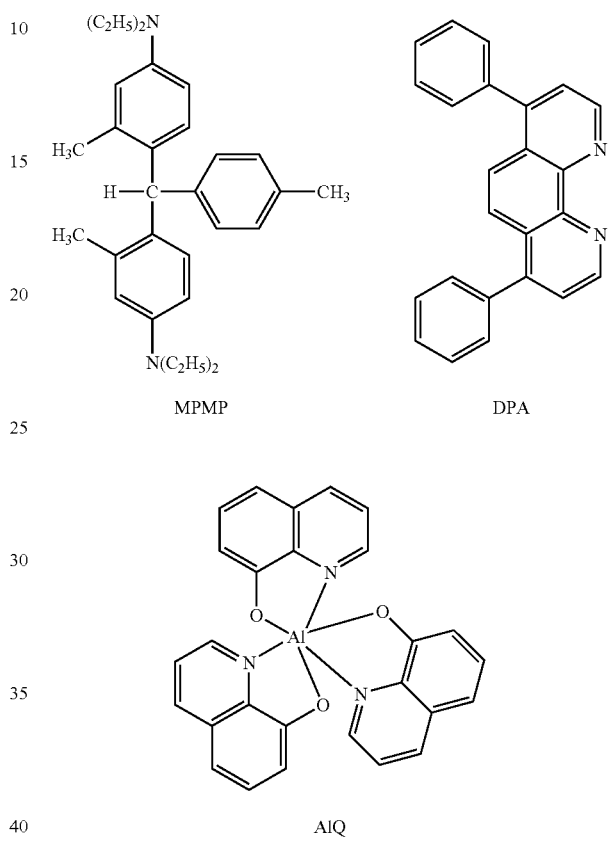

The (x,y) color coordinate is based on 1931 convention. The compound was deposited as a neat film. The electroluminescence spectrum shows a peak at 450 nm, but with a long tail, presumably due to aggregation in the neat film. This long tail could be removed if the compound is used as guest in a guest-host emitter layer.

TABLE I

Device configurations and efficiency of OLED device using Chrysene of Example 2 as the Emitter

| Hole transport material | Electron transport material | Device configuration | Efficiency (cd/A) | Radiance (cd/m2) | Peak wavelength (nm) | Color coordinates |
|---|---|---|---|---|---|---|
| MPMP | DPA | MPMP(330 Å)/ emitter(402 Å)/ DPA(104 Å)/ AlQ(303 Å)/ LiF(10 Å)/ Al(505 Å) | 1.5 | 500 | 450 | (0.23, 0.35) |

Note that not all of the activities described above in the general description or the examples are required, that a portion of a specific activity may not be required, and that one or more further activities may be performed in addition to those described. Still further, the order in which activities are listed is not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

In some embodiments, the invention herein can be construed as excluding any element or process step that does not materially affect the basic and novel characteristics of the composition or process. Additionally, in some embodiments, the invention can be construed as excluding any element or process step not specified herein.

The use of numerical values in the various ranges specified herein is stated as approximations as though the minimum and maximum values within the stated ranges were both being preceded by the word "about." In this manner slight variations above and below the stated ranges can be used to achieve substantially the same results as values within the ranges. Also, the disclosure of these ranges is intended as a continuous range including every value between the minimum and maximum average values including fractional values that can result when some of components of one value are mixed with those of different value. Moreover, when broader and narrower ranges are disclosed, it is within the contemplation of this invention to match a minimum value from one range with a maximum value from another range and vice versa.

What is claimed is:

1. An organic electronic device comprising:
a. a first electrical contact layer;
b. a layer comprising a composition of Formula I

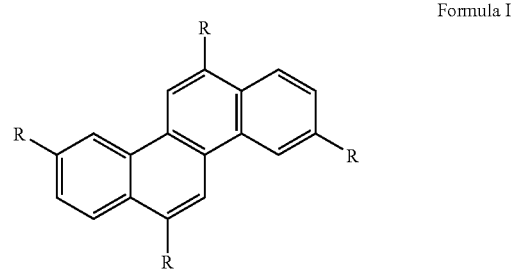

Formula I wherein each R is 4-t-butyl phenyl; and
c. a second electrical contact layer.

2. An organic electronic device comprising:
a. a first electrical contact layer;
b. a layer comprising a composition of Formula I

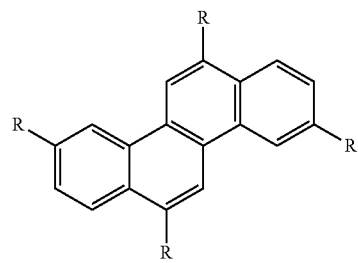

R is 2,4,6-trimethylphenyl; and
c. a second electrical contact layer.

* * * * *